(12) United States Patent
Graham

(10) Patent No.: US 6,341,688 B1
(45) Date of Patent: Jan. 29, 2002

(54) APPARATUS AND METHOD FOR DENTURE CLEANING AND STORAGE

(76) Inventor: Sandra P. Graham, 155 Magnolia Walk La., College Park, GA (US) 30349

( * ) Notice: Subject to any disclaimer, the term of this patent is extended or adjusted under 35 U.S.C. 154(b) by 0 days.

(21) Appl. No.: 09/687,919

(22) Filed: Oct. 14, 2000

Related U.S. Application Data

(63) Continuation of application No. 09/455,427, filed on Dec. 6, 1999, now abandoned.

(51) Int. Cl.[7] .......................... B65D 81/22; B65D 33/01; B65D 33/17; B65D 30/20; B08B 3/08
(52) U.S. Cl. .......................... 206/63.5; 134/34; 134/42; 134/201; 206/207; 383/63; 383/100; 383/120
(58) Field of Search .................. 206/63.5, 205, 206/207; 134/34, 42, 93, 137, 182, 184, 201; 383/63, 65, 100, 120; 433/216

(56) References Cited

U.S. PATENT DOCUMENTS

| | | |
|---|---|---|
| 3,802,919 A | 4/1974 | Saffir |
| 4,211,330 A | 7/1980 | Strock |
| 4,666,037 A | 5/1987 | Weissman |
| 4,775,318 A | 10/1988 | Breslin |
| 4,881,560 A | 11/1989 | Blank et al. |
| 4,903,718 A | 2/1990 | Sullivan |
| 5,184,718 A | 2/1993 | Albert |
| 5,240,415 A | 8/1993 | Haynie |
| 5,249,674 A | 10/1993 | Lepie |
| 5,346,061 A | 9/1994 | Newman et al. |
| 5,440,774 A | 8/1995 | Cole |
| RE35,034 E | 9/1995 | Albert |
| 5,549,201 A | 8/1996 | Braude |
| 5,678,580 A | 10/1997 | Sherman |
| 5,689,866 A | * 11/1997 | Kasai et al. ............... 383/63 X |
| 5,709,479 A | * 1/1998 | Bell ........................ 383/170 X |
| 5,996,800 A | * 12/1999 | Pratt ....................... 383/103 X |
| 6,167,597 B1 | * 1/2001 | Malin ....................... 383/63 X |

* cited by examiner

*Primary Examiner*—Bryon P. Gehman
(74) *Attorney, Agent, or Firm*—Joel D. Myers; Myers & Associates Intellectual Property Law P.C.

(57) ABSTRACT

Storage and cleaning apparatus for dentures comprising a plastic bag, the plastic bag including two ends, a top end and a bottom, and two side edges, a first side edge and a second side edge, and the plastic bag also including a triage of reusable seals, the triage being located near the top end and including an upper seal, a middle seal, and a lower seal, each of the seals including a male portion and a female portion, each of the seals extending parallel to each other and located approximately 1 centimeter to ½ inch from each other. In addition, the apparatus includes a cleaning agent assembly, the assembly being located on the inside of the plastic bag. The apparatus also includes a release valve incorporated into a side edge of the plastic bag, and includes pleating located on the lower half of each side edge of the plastic bag.

14 Claims, 3 Drawing Sheets

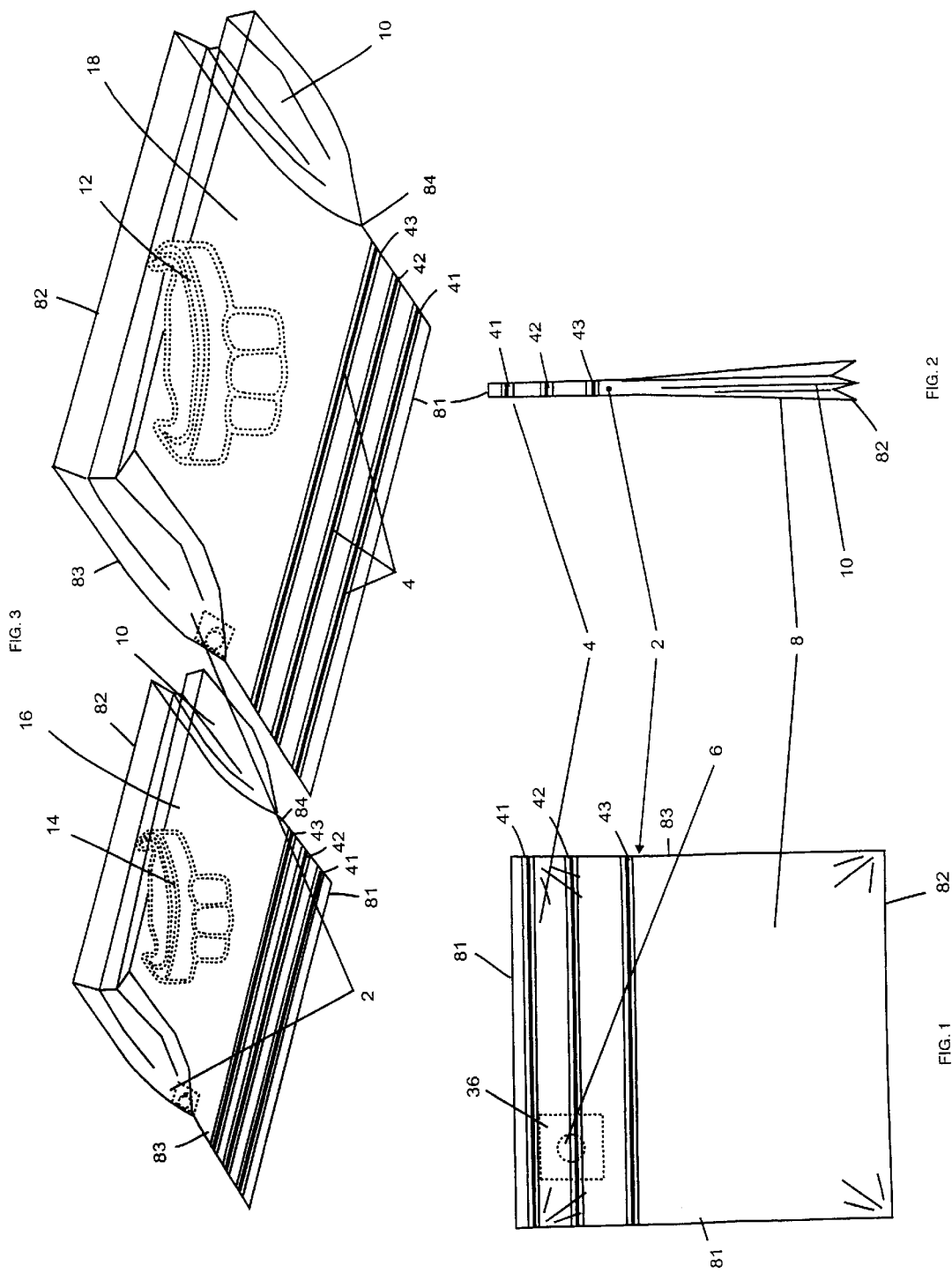

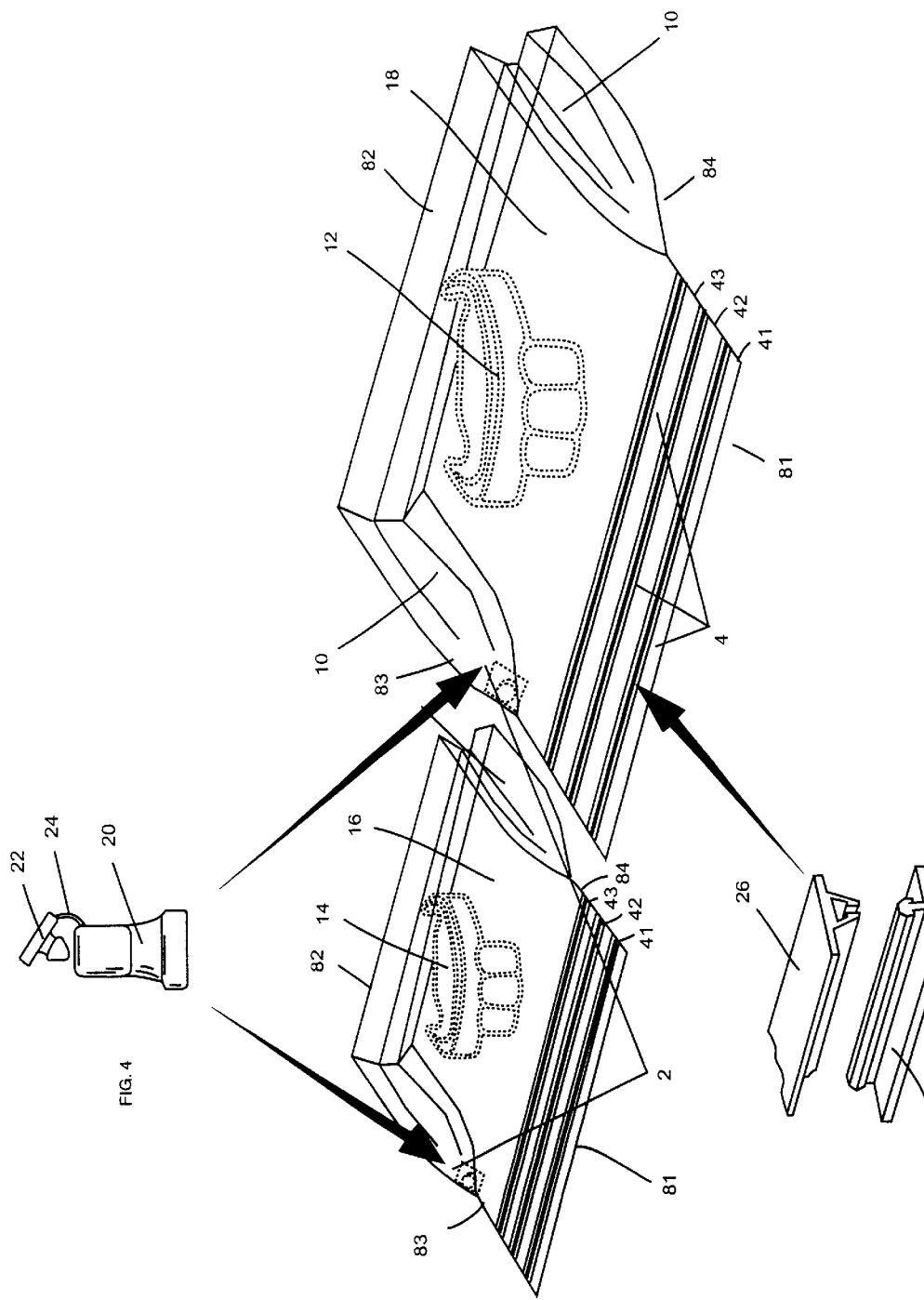

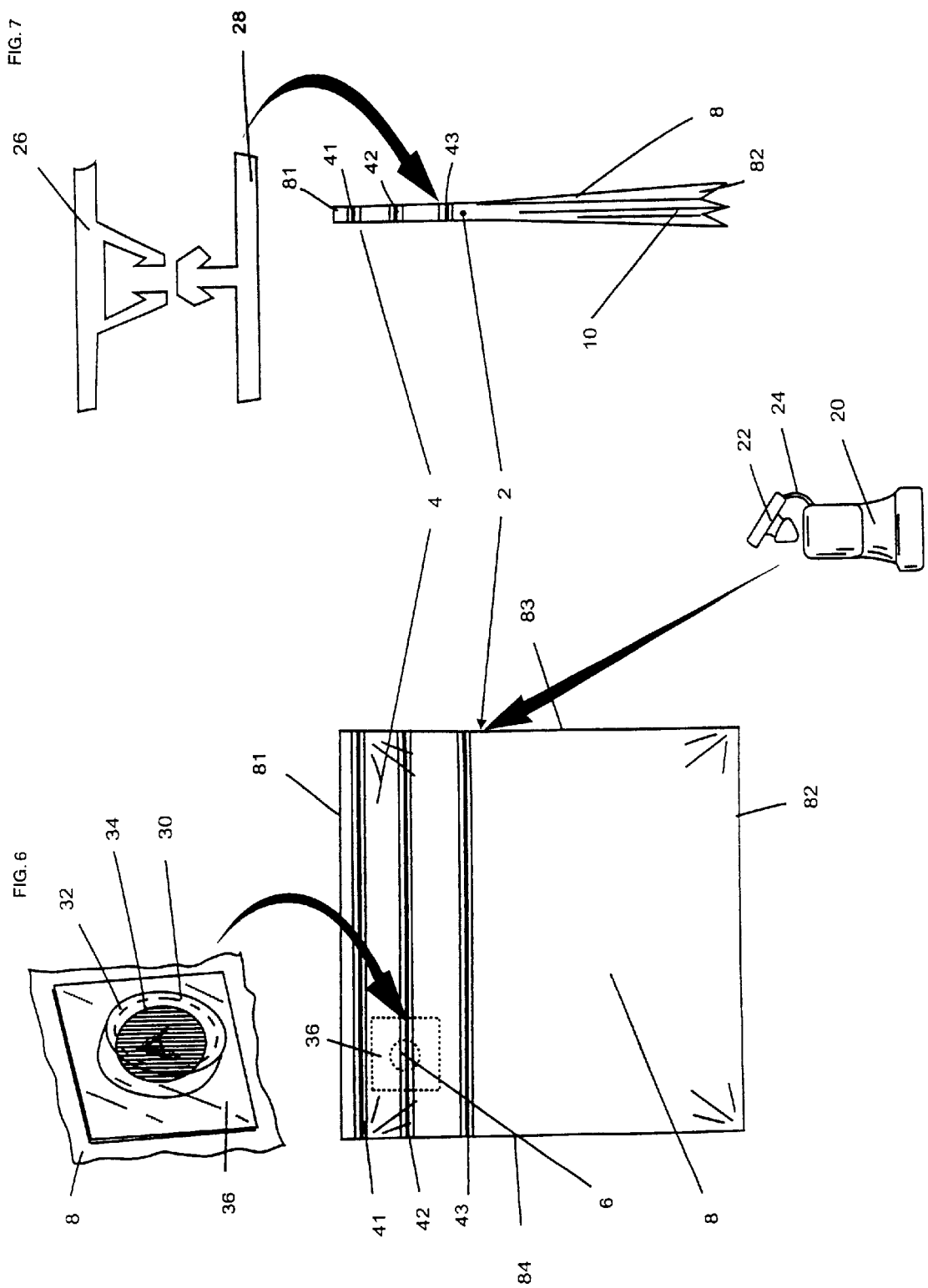

APPARATUS AND METHOD FOR DENTURE CLEANING AND STORAGE

PRIORITY

This non-provisional application is a continuation application of application Ser. No. 09/455,427 filed on Dec. 6, 1999, now abandoned, and claims the priority benefit thereof.

TECHNICAL FIELD

The present invention relates to a denture storage device and more particularly to a pleated plastic bag for denture storage having tongue-and-groove style seals and an enclosed cleaning agent packet.

BACKGROUND OF THE INVENTION

A wide variety of dental hygiene devices exist in the prior art. However, most of these devices incorporate the use of dental floss or are designed for use with natural teeth. One example of such prior art is U.S. Pat. No. 5,678,580 to Sherman. This device is a dental floss holder and dispenser sized and shaped to look like a credit card housed within a protective case. The protective case surrounds the floss holder and has one openable end allowing movement of the floss holder in and out of the protective case. The holder is provided with a supply of dental floss, preferably wound from side edge to side edge and about the middle section thereof.

U.S. Pat. No. 5,549,201 to Braude discusses a plurality of packages of dental floss with a plurality of separate elongate enclosures. Each elongate enclosure has length at least nine times as great as width with a piece of dental floss individually sealed therein.

U.S. Pat. 5,440,774 to Cole discloses a compact disposable teeth cleaning kit that can be carried easily in a purse or pocket. The kit includes a disposable finger mount, substantially cylindrical elastic sheath toothbrush having an open end and a closed end. The sheath is adapted to be rolled up or furled from its open end towards its closed end thereby creating a compact storage configuration wherein the full portion of the sheath forms a substantially angular peripheral rim with the end portion of the sheath spanning the area and circle by the rim. The end portion of the sheath is provided with brush means, such as protruding bristles that are adapted to clean the teeth of user when applied with a brushing motion thereto.

U.S. Pat. No. 5,346,061 to Newman, et al., discloses a dental treatment system with a flexible plastic outer container and a smaller, readily burstable thin film plastic inner container fixedly positioned in the outer container. The outer pouch is sealed with a foam dental treatment applicator therein. The inner container can be punctured in order to release the treatment solution, soaking the applicator. The bag is torn or cut open to allow removal of the treated applicator.

U.S. Pat. No. 5,249,674 to Lepie discloses a personal hygiene apparatus having a folded matchbook-like structure. A plurality of individually packaged dental floss members are detachably secured to the structure with pointed means for removing food particles from a user's teeth integral with the matchbook light structure and at least one abrasive material means detachably secured to the structure for manicuring a user's nails.

U.S. Pat. No. 5,240,415 to Haynie is a dental bleach system and method whereby the dental professional is provided with a predetermined quantity of fumed silica and a pre-measured volume of hydrogen peroxide solution wherein the hydrogen peroxide solution is mixed with the fumed silica immediately prior to application to the dental stain. Both the fumed silica and hydrogen peroxide are provided in the single-use kit having a tray and a removable cover. The container for the fumed silica serves as a mixing chamber. The hydrogen peroxide solution is contained in an ampoule that is carried in a recess in the tray. A spatula is also provided to mix the hydrogen peroxide and the fumed silica to form a paste and then apply the paste to a dental surface.

U.S. Pat. No. 5,184,718 to Albert and reissued Patent 35,034 to Albert disclose a disposable container adapted for single-use storing and cleaning of dentures. The container includes its own supply of cleanser.

U.S. Pat. No. 4,881,560 to Blank et al., discusses a thin dental floss dispenser having a credit card-like format, similar to the one disclosed in U.S. Pat. No. 4,327,755. The dispenser includes a base panel having a peripheral ridge defining a shallow well with a substantially flat bottom. A flattened supply coil of dental floss is located in the well and covered by a panel, marginally bonded to the ridge of the base panel, matching therewith.

U.S. Pat. No. 4,775,318 to Breslin discloses a storage means wherein the body has an upper section and a lower section, each section of the body having an extending portion providing a plurality of tooth elements corresponding to the upper teeth and lower teeth of a subject.

U.S. Pat. No. 4,666,037 to Weissman discloses a protective carrier for a dental model used in the production of a dental prosthesis. The carrier includes three hinged sections wherein the sections can be folded over each other to close the carrier.

U.S. Pat. No. 4,211,330 to Strock discloses an oral health and hygiene kit having a length of flexible liquid pervious material having a pocket for containing the finger.

As can be seen from the prior art, there are no denture cleaning devices that are designed specifically to be portable thereby permitting an individual to properly transport, clean and store a pair of dentures while traveling. The prior art provides various storage or use devices for dental floss and various cleaning agents or devices that are to be used on natural teeth, either by an individual in the privacy of their own home or by a dental professional.

The prior inventions that discuss dentures do not relate to an invention combining a portable storage mechanism for dentures with an incorporated cleaning agent. In addition, none of the prior art includes an incorporated cleaning agent in combination with an incorporated air valve thereby allowing the release of pressure that may form from the dissolving and interaction of the cleaning agent with water. The present invention combines the characteristic of disposability with a portable storage device for dentures, incorporating a cleaning agent therein, wherein the denture storage device also functions to contain the dissolved cleaning agent solution when denture cleaning is desired.

BRIEF SUMMARY OF THE INVENTION

The present invention is a heavy, 3 mil plastic bag including a top end, a bottom end, a first side edge and a second side edge. The top end of the plastic bag includes three tongue-and-groove style seals, commonly known in the art by the trademark ZIPLOCK, that run from the first side edge of the plastic bag to the second side edge of the plastic bag. The three tongue-and-groove style seals are parallel to each other and include an upper seal, a middle seal, and a lower seal.

The first side edge of the plastic bag includes a release valve fixedly mounted onto the bag. This release valve is a one-way air release mechanism to allow air within the plastic bag to escape. The release valve includes an air valve tube, an air valve tip and a plastic connector. The air valve tube is a hollow tube. The air valve tip is a small piece of plastic which prevents air from being lost when the air valve tip is connected to the air valve tube. The plastic connector is a small piece of plastic which connects the air valve tip to the air valve tube and prevents the air valve tip from being lost when the air valve tip is not connected to the air valve tube.

The plastic bag includes a cleaning agent assembly fixedly mounted on the plastic bag in between the upper seal and the middle seal on the inside of the bag. The cleaning agent assembly includes an attached plastic square, a cleaning agent packet, a cleaning agent, and a perforated plastic ring on the surface of the cleaning agent packet. The upper and middle seals may extend through the attached plastic square wherein the plastic square should be attached to the plastic bag before the seals are created. The upper seal and middle seal cannot contact the area of the perforated plastic ring or extend therethrough because after perforation thereof, the ring would prevent complete closure of the seal extending through the perforated plastic ring.

The cleaning agent packet in the cleaning agent assembly may be foil, plastic and/or paper. The attached plastic square is approximately one inch by one inch in diameter. The cleaning agent located within the cleaning agent packet is preferably a tablet.

Each of the three tongue-and-groove seals is composed of a male portion and a female portion. Both the male and female portions of the seals are preferably formed by the process of extrusion, but can also be formed by the process of plastic heat sealing.

Both the first edge and the second edge of the plastic bag are pleated near the bottom end of the bag. The pleats begin on each side edge of the plastic bag approximately halfway between the top end and the bottom end. The pleats increase in depth as they move toward the bottom end. The pleats are included in the plastic bag to allow the plastic bag to expand if water is placed within the bag.

The plastic bag for this invention comes in one of two sizes. The first size is termed the small size, and is designed for a partial set of dentures. The small size measures approximately three inches by three inches. The large size is designed to hold a full set of dentures. The large size is approximately five inches by five inches.

It is therefore an object of this invention to provide a new and improved portable storage device for dentures.

It is another object of this invention to provide a new and improved portable storage device for dentures wherein the device can also be used to store a set of dentures being cleaned.

It is still another object of this invention to provide a new and improved portable storage device incorporating a cleaning agent that can be activated at the option of the user.

It is yet another object of invention to provide a new and improved portable storage device for dentures that is leak proof.

It is yet another object of this invention to provide a new and improved portable storage device for dentures that includes a release valve to release pressure therein.

Other objects, features and advantages of the present invention will become more readily apparent from the detailed description of the preferred embodiment when considered with the attached drawings and appended claims.

BRIEF DESCRIPTION OF THE DRAWINGS

FIG. 1 is a front view of a denture cleaning and storage device according to a preferred embodiment of the present invention.

FIG. 2 is a side view of the denture cleaning and storage device of FIG. 1.

FIG. 3 is a perspective view of denture cleaning and storage device of FIG. 1 showing two sizes thereof.

FIG. 4 is a side view of a release valve according to a preferred embodiment of the present invention.

FIG. 5 is a perspective view of a tongue-and-groove seal according to a preferred embodiment of the present invention showing a male portion disengaged from a female portion and showing the preferred location thereof on a denture cleaning and storage device.

FIG. 6 is a perspective view of a cleaning agent assembly according to a preferred embodiment of the present invention showing the assembly fixedly mounted on the inside of a plastic bag between an upper seal and a middle seal.

FIG. 7 is a side view of the tongue-and-groove seal of FIG. 5 showing a male portion disengaged from a female portion and showing a preferred location thereof on a denture cleaning and storage device.

DETAILED DESCRIPTION OF THE PREFERRED AND ALTERNATE EMBODIMENTS

Referring now to FIG. 1, plastic bag 8 preferably includes upper seal 41, middle seal 42, lower seal 43, release valve 2, cleaning agent assembly 6 and pleats 10.

Plastic bag 8 contains top end 81, bottom end 82, first edge 83 and second side edge 84. Top end 81 of plastic bag 8 preferably includes upper seal 41, middle seal 42 and lower seal 43, preferably tongue-and-groove type seals that extend from first side edge 83 to second side edge 84 of plastic bag 8. Upper seal 41, middle seal 42, and lower seal 43 extend parallel to each other and are preferably positioned approximately one centimeter to one-half inch from each other.

First side edge 83 of plastic bag 8 preferably includes release valve 2 fixedly mounted onto plastic bag 8. Release valve 2 is a one-way air release mechanism to allow air within plastic bag 8 to escape. Release valve 2 is comprised of air valve tube 20, air valve tip 22 and plastic connector 24. Air valve tube 20 is a hollow tube. Air valve tip 22 is preferably removably attached to the top of air valve tube 20. Plastic connector 24 is preferably a small piece of plastic which connects air valve tip 22 to air valve tube 20 thereby preventing the loss of air valve tip 22 when not connected to air valve tube 20.

Plastic bag 8 includes cleaning agent assembly 6 preferably fixedly mounted on plastic bag 8 in between upper seal 41 and middle seal 42. Cleaning agent assembly 6 is mounted on the inside of plastic bag 8. Cleaning agent assembly 6 preferably includes attached plastic square 36, cleaning agent packet 32, cleaning agent 34 and perforated ring 30, wherein perforated ring 30 is preferably positioned on the surface of cleaning agent assembly 6. Upper seal 41 and middle seal 42 may extend through attached plastic square 36, however attached plastic square 36 must be attached before the seals are created. Upper seal 41 and middle seal 42 cannot touch or extend through the area of perforated plastic ring 30, because following the perforation of plastic ring 30, a seal extending therethrough would not provide a complete seal for contents within bag 8.

Cleaning agent packet 32 in cleaning agent assembly 6 is preferably composed of plastic. One skilled in the art will recognize that, while plastic is the preferred material for cleaning agent packet 32, other materials may also be utilized, such as, for exemplary purposes only, foil or paper. Attached plastic square 36 is preferably approximately one inch by one inch in diameter. Cleaning agent 34 is located within cleaning agent packet 32 and is preferably a tablet.

Each seal has a male portion 28 and female portion 26. Both male portion 26 and female portion 28 are preferably formed by the process of extrusion, but may alternately be formed by the process of plastic heat sealing.

Both first side 83 and second side 84 are pleated near the bottom of plastic bag 8. Pleats 10 begin on each side of plastic bag 8 preferably approximately halfway between top end 81 and bottom end 82. Pleats 10 increase in depth as pleats 10 extend from the center of plastic bag 8 to bottom end 82.

Plastic bag 8 preferably includes two sizes. Small size 16 is dimensioned to receive a partial set of dentures and is preferably approximately three inches by three inches. Large size 18 is dimensioned to receive a full set of dentures and is preferably approximately five inches by five inches.

In use, a user places a set of dentures 12 into large size 18 of plastic bag 8. Alternatively, a user could place a partial set of dentures 14 into small size 16 of plastic bag 8. User then presses together both sides of upper seal 41, middle seal 42 and lower seal 43, thereby forcing male portion 28 and female portion 26 of each seal to removably attach to each other. After full set of dentures 12 or partial set of dentures 14 are placed into plastic bag 8, plastic bag 8 is conveniently portable, allowing the user to transport dentures as desired.

If denture cleaning is desired, the user substantially fills plastic bag 8 with water. Both sides of upper seal 41, middle seal 42, and lower seal 43 are pressed together, thereby forcing male portion 28 and female portion 26 of each seal to removably attach to each other and properly seal the contents of plastic bag 8. The backside of each cleaning agent assembly 6 is pressed, thereby forcing said cleaning agent 34 to be pushed through perforated plastic ring 30 and into the water in plastic bag 8. Cleaning agent 34 mixes with the water in plastic bag 8 thereby providing a cleaning solution for a full set of dentures 12 or a partial set of dentures 14. Once the user is content with denture cleanliness, water is removed from plastic bag 8 revealing a clean set of dentures.

During the cleaning process, gases may result from the chemical reactions in plastic bag 8 thereby causing inflation of plastic bag 8. If plastic bag 8 begins to over-inflate, release valve 2 is activated by opening up air valve tip 22 thereby allowing excess air within plastic bag 8 to escape. After excess air is removed, air valve tip 22 is replaced onto air valve tube 20, thereby re-closing off contact between the contents of plastic bag 8 and the outside air.

What is claimed is:

1. A denture storage and cleaning apparatus comprising:
   a bag having a first open end, a first side edge, a second side edge and an inner surface, said bag dimensioned for receiving at least one denture to be cleaned;
   means for sealing said open end of said bag;
   a cleaning agent receptacle carried within said bag; and
   a cleaning agent received within said cleaning agent receptacle, wherein introduction of a liquid into said bag and introduction of said liquid to said cleaning agent initiates an independently functioning, self-contained cleansing procedure of said at least one denture.

2. The denture storage and cleaning apparatus of claim 1 wherein said means for sealing said open end of said bag is at least one reusable seal, said at least one reusable seal positioned proximate to said first open end wherein each said seal includes a male portion and a female portion, said male portion and said female portion extending approximately from said first side edge of said bag to said second side edge of said bag.

3. The denture storage and cleaning apparatus of claim 2, wherein said at least one reusable seal comprises a plurality of reusable seals having a first upper seal, a second middle seal and a third lower seal, said first upper seal positioned proximate to said first end of said bag, said third lower seal positioned proximate to said first seal and said middle second seal positioned therebetween.

4. The denture storage and cleaning apparatus of claim 1, wherein said cleaning agent is an effervescent tablet.

5. The denture storage and cleaning apparatus of claim 1, wherein said cleaning agent receptacle comprises perforations, said perforations dimensioned to permit passage of said cleaning agent therethrough.

6. The denture storage and cleaning apparatus of claim 1, wherein said cleaning agent receptacle is carried on said inner surface of said bag.

7. A disposable denture storage and cleaning device comprising:
   a plastic bag having at least one reusable sealing means, a first end, a second end, a first side edge, a second side edge and an inner surface;
   a cleaning agent;
   a cleaning agent container having a substantially flat outer surface wherein perforations in said outer surface define a user-activated means for disbursing said cleaning agent into said bag, wherein said cleaning agent container further comprises a semi-rigid plastic ring, and wherein said perforations define a substantially circular shaped user-activated aperture within said plastic ring; and
   a means for releasing gas from said bag, said means carried by said plastic bag, extending therethrough.

8. The disposable denture storage and cleaning device of claim 7, wherein said reusable sealing means is a plurality of tongue-and-groove seals.

9. The disposable denture storage and cleaning device of claim 7, wherein said cleaning agent is an effervescent tablet.

10. The disposable denture storage and cleaning device of claim 7, wherein said cleaning agent container is carried on said inner surface of said bag.

11. The disposable denture storage and cleaning device of claim 7, wherein said means for releasing gas from said bag is a release valve comprising a hollow air valve tube having a hingedly attached air valve tip.

12. The disposable denture storage and cleaning device of claim 7, wherein said second end of said bag is pleated and wherein said pleats are formed to allow expansion of said bag.

13. The method of storing and cleaning dentures comprising the steps of:
   a) obtaining a disposable denture storage and cleaning device with a resealable plastic bag, a cleaning agent, said cleaning agent held within a receptacle within said bag, said receptacle having perforations defining a user-activated means for disbursing said cleaning agent into said bag and said receptacle having a semi-rigid plastic ring, where in said perforations define a substantially circular shaped user-activated aperture within said plastic ring, and a release valve;

b) placing at least a partial set of dentures into said bag;

c) filling said bag with liquid;

d) sealing said bag;

e) pressing said perforations on said cleaning agent receptacle thereby disbursing said cleaning agent into said bag wherein said cleaning agent mixes with said liquid and cleans the denture; and f) emptying liquid from said bag and removing clean denture.

14. A storage and cleaning apparatus for dentures comprising a plastic bag, said bag including two ends, a top end and a bottom end, and two side edges, a first side edge and a second side edge, and said bag also including:

a triage of reusable seals, said triage being located near said top end and including an upper seal, a middle seal, and a lower seal, each of said seals including a male portion and a female portion, each of said seals starting at said first side edge of said plastic bag and running to said second side edge of said plastic bag, and each of said seals running parallel to each other and located approximate 1 meter to ½ inch from each other, a cleaning agent assembly, said assembly being attached to the inside of said plastic bag and including a cleaning agent packet, a cleaning agent located within said packet, a perforated plastic ring located on said cleaning agent packet, an attached piece of plastic, said piece of plastic being square, approximately 1 inch by 1 inch, and said piece of plastic affixing said cleaning agent packet to the inside of said plastic bag, a release valve, said valve being fixedly connected to a side edge of said plastic bag and including an air valve tube, said tube being hollow, an air valve tip, and a connector designed to attach said air valve tube to said air valve tip, and pleating, said pleating being located on the first side edge and second side edge of said plastic bag, said pleating beginning on each side edge approximately half way between said top end and said bottom end of said plastic bag.

\* \* \* \* \*